United States Patent [19]

Kishore

[11] Patent Number: 4,562,151

[45] Date of Patent: Dec. 31, 1985

[54] STABILIZATION OF L-PHENYLALANINE AMMONIA-LYASE ENZYME

[75] Inventor: Ganesh M. Kishore, St. Peters, Mo.

[73] Assignee: Monsanto Company, St. Louis, Mo.

[21] Appl. No.: 529,434

[22] Filed: Sep. 6, 1983

[51] Int. Cl.[4] .................. C12P 13/22; C12P 13/06; C12P 13/00; C12N 9/96; C12N 9/88
[52] U.S. Cl. .................. 435/108; 435/116; 435/128; 435/188; 435/232
[58] Field of Search .............. 435/188, 108, 232, 116, 435/128

[56] References Cited

U.S. PATENT DOCUMENTS 4,248,704  2/1981  Marconi et al. ............. 435/232

FOREIGN PATENT DOCUMENTS 26197  3/1983  Japan .

OTHER PUBLICATIONS

Yamada et al. in Applied and Environmental Microbiology, vol. 42, No. 5, pp. 773–778 (1981).
Tanaka et al., *J. Biochem.*, 81, pp. 963–970, (1977).
Hanson et al., *Biochemistry*, 18(8), pp. 1431–1438, (1979).
Birnbaum et al., *Biotechnology Letters*, 3 (8), pp. 393–400, (1981).
Douzou et al., *Adv. in Protein Chemistry*, 32, p. 79, (1978).
Yasumatsu et al., *Agr. Biol. Chem.* 29(7), pp. 665–671, (1954).
Ruis et al., *Phytochemistry*, 10, pp. 2627–2631, (1971).

*Primary Examiner*—Lionel M. Shapiro
*Attorney, Agent, or Firm*—Dennis R. Hoerner, Jr.; James W. Williams, Jr.

[57] ABSTRACT

A process for the synthesis of L-phenylalanines and analogues thereof from trans-cinnamate, ring substituted trans-cinnamates or various acrylate derivatives and ammonia or an ammonia donor in the presence of L-phenylalanine ammonia-lyase enzyme and a desensitizing agent such as polyhydric alcohols and polyethylene glycol-(400) is disclosed. The process embraces the discovery that compounds such as polyhydric alcohols and polyethylene glycol-(400) desensitize the L-phenylalanine ammonia-lyase enzyme to substantially higher substrate concentrations than practiced heretofore. In addition, polyhydric alcohols and polyethylene glycol-(400) substantially enhance the instantaneous rate of reaction and inhibit inactivation of the L-phenylalanine ammonia lyase enzyme over longer reaction periods.

18 Claims, 1 Drawing Figure

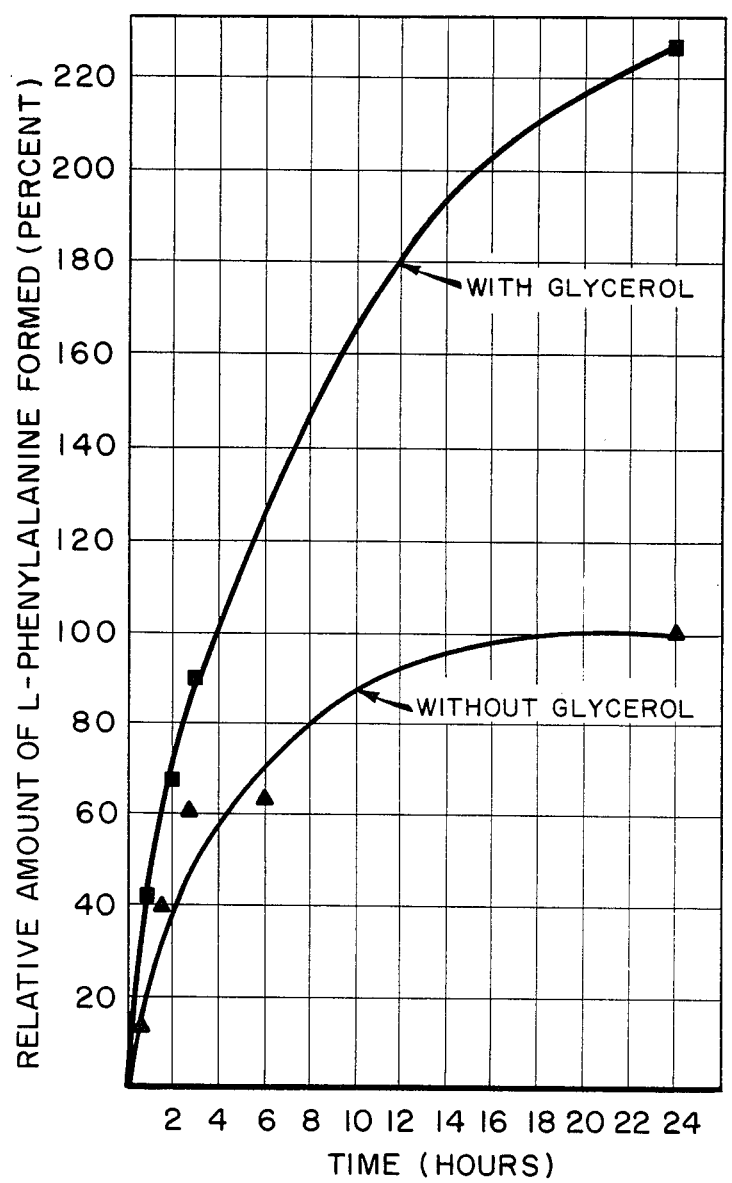

STABILIZATION OF L-PHENYLALANINE AMMONIA-LYASE ENZYME

BACKGROUND OF THE INVENTION

The present invention relates to the synthesis of L-phenylalanine and analogues thereof and more particularly to a process wherein L-phenylalanine ammonia-lyase enzyme is desensitized to elevated concentrations of trans-cinnamate, ring substituted trans-cinnamates and various acrylate derivtives.

The synthesis of L-phenylalanine from trans-cinnamate and ammonia or an ammonia donor using L-phenylalanine ammonia-lyase enzyme has been disclosed in several publications and patents. However, these prior attempts to effect this reaction have been, as a practical matter, unsuitable for commercial scale processing. The reaction between trans-cinnamate and ammonia to produce L-phenylalanine is thermodynamically unfavorable. The reported equilibrium constant value of 4.7 M necessitates the use of ammonia concentrations greater than 4.7 M to achieve a trans-cinnamate to L-phenylalanine conversion of more than fifty percent. Moreover, L-phenylalanine ammonia-lyase is inhibited by cinnamate even at low cinnamate concentration. Phenylalanine ammonia-lyase activity at 250 mM cinnamate concentration has been reported to be only about one percent of the activity at a concentration of 50 mM. Hence, processes disclosed heretofore require a dilute cinnamate concentration which unavoidably increases product recovery cost.

It is the overall object of the present invention to provide a process having increased productivity.

Accordingly, it is an object of the present invention to provide a process having an increased rate of reaction.

It is another object of the present invention to provide a process capable of operating at much higher cinnamate concentrations than processes disclosed heretofore.

It is yet another object of the present invention to provide a process wherein L-phenylalanine ammonia-lyase enzyme is desensitized to elevated concentrations of trans-cinnamate, ring substituted trans-cinnamates and various acrylate derivatives.

These and other objects, features, and advantages of the present invention will be evident to one skilled in the art from the following description.

SUMMARY OF THE INVENTION

The present invention provides an improved process for the synthesis of L-phenylalanine and analogues thereof from trans-cinnamate, ring substituted trans-cinnamates or various acrylate derivatives and ammonia or an ammonia donor using L-phenylalanine ammonia-lyase enzyme. The present invention embraces the discovery that compounds such as polyhydric alcohols and polyethylene glycol-(400) desensitize the L-phenylalanine ammonia-lyase enzyme to subtantially higher substrate concentrations than practiced heretofore. Furthermore, polyhydric alcohols and polyethylene glycol-(400) substantially enhance the instantaneous rate of reaction and inhibit inactivation of the L-phenylalanine ammonia-lyase enzyme over longer reaction periods. As a result, the process of the present invention permit higher enzyme payloads, higher product concentrations and therefore lower product recovery cost.

BRIEF DESCRIPTION OF THE DRAWINGS

The sole FIGURE is a graphical illustration of the effect of glycerol on the rate of L-phenylalanine formation.

DETAILED DESCRIPTION OF THE PREFERRED EMBODIMENTS

Early work in enzyme chemistry was impeded by the tendency of aqueous based purification procedures to render the purified enzyme inactive. While not fully understood, it is believed that the aqueous solvent affects the hydrophobic regions of the enzyme thereby changing the conformational shape of the enzyme molecule. Conformational change, in some cases, causes irreversible denaturation thereby rendering the enzyme inactive. Protein chemists subsequently found that if a polyhydric alcohol such as glycerol is added to the aqueous purification mixture deactivation would not occur during the purification procedure. Various mechanisms are proposed to account for this inactivation inhibition, but the actual mechanism has not been determined, see *Advances in Protein Chemistry*, 32 (1978) p. 79. While the stabilizing effect of polyhydric alcohols on the activity of aqueous enzyme solutions have been disclosed, prior teachings in this area have not disclosed the enhanced activity and desensitization effects of the present invention, for example see Yasumatsu et al., "Stabilities of Enzymes in Polyhydric Alcohols", *Agr. Biol. Chem.*, 29(7), (1965), pp 665-14 671.

The present invention embraces the surprising discovery that addition of desensitizing agents such as polyhydric alcohols or polyethylene glycol-(400) to the aqueous reaction mixture substantially desensitizes the L-phenylalanine ammonia-lyase enzyme to substantially higher substrate concentrations than practiced heretofore. It should be understood that by "polyhydric alcohol" is meant a compound containing more than two hydroxyl groups. This unexpected result permits the reaction to be run at significantly higher substrate concentrations. The higher substrate concentrations of the present invention result in higher enzyme payloads, higher product concentrations and lower product recovery cost. For purposes of the present invention, L-phenylalanine ammonia-lyase enzyme should be considered to be desensitized when the enzyme activity is greater in the presence of a desensitizing agent than in the absence of the agent for a fixed set of reaction conditions such as substrate concentration, etc.

It should be understood that since L-phenylalanine ammonia-lyase enzyme is substrate specific for trans-cinnamates, cinnamate concentrations referred to in this specification will be for a cinnamate mixture comprising essentially pure trans-cinnamate isomer from trans-cinnamic acid or a salt of trans-cinnamic acid exclusive of esters. It is well known that L-phenylalanine ammonia-lyase is also active on various ring substituted trans-cinnamic acids having substituents such as hydroxy, halogen and nitro radicals, see H. Ruis et al., *Phytochemistry*, 10, 2627-14 2631 (1971) and Y. Tanaka et al., *J. Biochem.*, 81, 963–970 (1977). For example, amination of para-coumaric acid forms L-tyrosine and amination of caffeic acid forms 3,4 dihydroxy-L-phenylalanine commonly referred to as L-dopa. It is also known that L-phenylalanine ammonia-lyase is active on various acrylate derivatives. For example, amination of trans-3-(1,4 cyclohexadienyl) acrylic acid forms the phenylalanine analogue, 3-(1,4-cyclohexadienyl)-L-alanine, see Hanson et al., Biochemistry 18, 1431–1438 (1979). It should be understood that such ring substituted trans-cinnamates and acrylate derivatives are within the scope of the present invention. Accordingly, by "substrate" is meant trans-cinnamate, ring-substituted trans-cinnamates and acrylate derivatives which are known to undergo amination in the presence of ammonia or an ammonia donor and L-phenylalanine ammonia-lyase enzyme. By "ammonia donor" is meant an ammonia or ammonium compound which furnishes ammonia upon addition to the reaction mixture.

It should be evident to those skilled in the art that the enhanced process of the present invention is capable of using essentially any preparation of L-phenylalanine ammonia-lyase enzyme ranging from a purified enzyme preparation to whole cells containing L-phenylalanine ammonia-lyase enzyme. Microbial cells or plant cells containing L-phenylalanine ammonia-lyase enzyme are preferred since no preliminary purification is required. Examples of suitable microbial cells include, but are not limited to, Sporobolomyces roseus, Ustilago hordei, Rhodotorula glutinis, Rhodotorula teensis, Rhodotorula rubra, Fusarium oxysporum and Streptomyces verticillatus. It is further evident to those skilled in the art that L-phenylalanine ammonia-lyase enzyme from a particular source may not be active with all trans-cinnamates. For example, L-phenylalanine ammonia-lyase from plant cells, is generally specific for trans-cinnamate while L-phenylalanine ammonia-lyase enzyme from yeast and fungi can generally act on ring substituted trans-cinnamates. Accordingly, one needs to select the source of enzyme so that the enzyme is active on the particular trans-cinnamate or acrylate derivative of interest.

For conciseness, the following explanation and examples of the present invention are described with respect to L-phenylalanine ammonia-lyase enzyme from Rhodotorula glutinis cells (ATCC 15385) known to catalyze the reversible reaction between trans-cinnamate and an ammonia donor to form L-phenylalanine. To facilitate transport of substrate and product across the cell membrane about 3 to 5 microliters of polyethyleneglycol-p-isooctylphenylether per gram wet weight of cells is preferably added to the microbial cell suspension. It should be understood that the addition of polyethylene glycol-p-isooctylphenylether or other detergents which increase the permeability of cell membranes is not necessary for practice of the present invention.

The effects of increasing cinnamate concentrations on the reactivity of L-phenylalanine ammonia-lyase enzyme with and without the addition of glycerol are shown in Table I.

TABLE I

| Relative Effect of Cinnamate Concentration on L-Phenylalanine Ammonia-Lyase Activity | | | |
|---|---|---|---|
| Cinnamate Conc. (mM) | PAL Activity with glycerol | PAL Activity without glycerol | |
| 30.0 | —(1) | 47(2) | —(3) |
| 46.1 | 100 | — | 100 |
| 60.0 | — | 100 | — |
| 90.0 | — | 70 | — |
| 140.0 | 100 | — | 64 |
| 150.0 | — | 33 | — |
| 185.0 | 75 | — | 33 |

TABLE I-continued

| Relative Effect of Cinnamate Concentration on L-Phenylalanine Ammonia-Lyase Activity | | |
|---|---|---|
| Cinnamate Conc. (mM) | PAL Activity with glycerol | PAL Activity without glycerol |
| 250.0 | 59 | 1 |

(1)glycerol concentration = 2.3 M, ammonia concentration = 6.8 M; pH of the reaction mixture = 11.2; temperature = 37° C.; concentration of R. glutinis cells = 90 mg/ml. Enzyme activity at 46.1 mM cinnamate was taken as 100.
(2)ammonia concentration = 6.8 M; pH of the reaction mixture = 11.2; temperature = 37° C.; concentration of R. glutinis cells = 90 mg/ml. Enzyme activity at 60.0 mM cinnamate was taken as 100.
(3)values listed are interpolated from those reported in Japanese Patent SHO 56 [1981]-26197; ammonia concentration = 15.4% (9 M); pH of the reaction mixture = 10.0; temperature = 30° C.

As shown in Table I, the presence of glycerol substantially desensitizes L-phenylalanine ammonia-lyase enzyme to higher concentration of cinnamate reactant. While not fully understood, cinnamate appears to have two distinct modes of binding on the L-phenylalanine ammonia-lyase enzyme. This is evidenced by the lack of change in enzyme activity when the cinnamate concentration is initially increased in the presence of glycerol. Desensitizing agents such as polyhydric alcohols are able to desensitize the inhibitory mode of binding under substantially higher cinnamate concentrations than practiced heretofore while not substantially affecting the affinity of the catalytic site for the trans-cinnamate reactant. In the absence of glycerol, an incremental increase in cinnamate concentration has been shown to result in a decrease in L-phenylalanine ammonia-lyase activity, see Japanese Patent SHO 56 [1981]- 26197. Heretofore, the reactivity of L-phenylalanine ammonia-lyase enzyme at 250 mM cinnamate was reported to be only about one percent of that measured at 50 mM. The desensitizing effect of glycerol embraced by the present invention permits the activity of the L-phenylalanine ammonia-lyase enzyme at 250 mM cinnamate to be about 60 percent of that measured at 50 mM.

While the process of the present invention is operable over a rather broad cinnamate concentration range, the preferred range is between about 100 mM. It should be understood that the optimal cinnamate concentration will depend on the pH and particular polyhydric alcohol utilized.

It should be further understood that while L-phenylalanine ammonia-lyase enzyme exhibits increased activity at higher temperatures such as 37° C., the enzyme does not exhibit a substantially higher degree of relative inactivation from increased concentrations of cinnamate in the presence of glycerol than that shown in Table I. While the enhanced process of the present invention is capable of operating between about 20° C. and 60° C., the preferred temperature range is between about 30° C. and 40° C.

Heretofore, the optimal pH for L-phenylalanine ammonia-lyase activity was reported to be about 10. However, this pH optimum was observed at a cinnamate concentration of only 50 mM since the enzyme was heretofore inhibited by higher cinnamate concentrations. It has been further discovered that at the higher cinnamate concentrations contemplated by the enhanced process of the present invention L-phenylalanine ammonia-lyase can be further desensitized by increasing the pH of the reaction mixture. The effect of pH on the reaction rate in the absence of any polyhydric alcohols is shown below in Table II.

TABLE II

Effect of pH on L-phenylalanine ammonia-lyase Activity at Elevated Cinnamate Concentrations

| Cinnamate Conc., mM | Relative Rate of L-phenylalanine Formation at pH 11.5 vs. pH 10.5, (%) |
| --- | --- |
| 68 | 45 |
| 135 | 152 |
| 202 | 200 |
| 270 | 125 |
| 337 | 250 |

Reaction rates were determined at pH 10.5 and 11.5 and the rates at pH 10.5 taken as 100. As shown in Table II, reaction rates were significantly higher at pH 11.5 compared with those measured at 10.5 for the same cinnamate concentration. These experiments indicate that desensitization of L-phenylalanine ammonia-lyase enzyme to cinnamate can be achieved, for the elevated cinnamate concentrations contemplated by the present invention, by increasing the pH of the reaction mixture above the heretofore reported optimal pH 10.

The process of the present invention is capable of operating over a rather broad pH range which is essentially defined by the stability of the L-phenylalanine ammonia-lyase enzyme. While the operable pH range is between about 9 and 12, the preferred pH range in the presence of polyhydric alcohols is about 11.0 and 11.5. The apparent optimal pH in the presence of glycerol is about 11.2.

The increased operating pH of the present invention permits a much simpler recovery procedure than possible heretofore. Since the preferred operating pH is well above the ammonium to ammonia pK' of 9.25, the unreacted ammonia can be easily removed by vacuum distillation. Removal of the ammonia causes the precipitation of most of the unreacted cinnamic acid in the reaction mixture. The L-phenylalanine can then be removed by standard isolation techniques.

Further experiments have shown that polyhydric alcohols, such as glycerol, have a substantial effect on the short-term activity of the L-phenylalanine ammonia-lyase enzyme in addition to a stabilizing effect on the long-term activity of the enzyme. The relative rates of L-phenylalanine formation from trans-cinnamate for a twenty-four hour period in the presence and absence of glycerol are plotted in the graph shown in the Figure. The reaction mixture consisted of 200 mM cinnamate, 6.0 M ammonia, 2.0 M glycerol and R. glutinis cells at pH 11.5 and 37° C. The final concentration of R. glutinis cells was approximately 90 mg/ml(wet weight). L-phenylalanine formation was determined by high pressure liquid chromatography. The amount of L-phenylalanine formed in twenty-four hours in the absence of glycerol was taken as 100.

As can be seen in the Figure, the L-phenylalanine ammonia-lyase enzyme in the absence of glycerol or any other polyhydric alcohol is essentially inactivated after 12 hours. The long term stabilizing effect of polyhydric alcohols can be easily observed by the substantial amount of L-phenylalanine formed during the 12 to 24 hr period in the presence of glycerol. One should also observe that the initial slope of the glycerol curve is significantly steeper than the control curve which lacks the addition of glycerol. The increased slope indicates a higher instantaneous rate of reaction in the presence of glycerol.

It should be understood that the above described experiments are provided to illustrate the practice of the present invention and are not intended to limit the scope of the present invention. Rather, one may use essentially any polyhydric alcohol in the process of the present invention. However, it should be evident to those skilled in the art that the effect of the polyhydric alcohol will vary with the species selected.

The effects of several common polyhydric alcohols are shown below in Table III.

TABLE III

Relative Effect of Polyhydric Alcohols on L-phenylalanine ammonia-lyase Activity

| Run | Polyhydric Alcohol | Conc. | PAL Enzyme Activity |
| --- | --- | --- | --- |
| 1 | control, none | — | 28 |
| 2 | glycerol | 0.72 M | 100 |
| 3 | D-mannitol | 0.43 M | 29 |
| 4 | D-sorbitol | 0.43 M | 74 |
| 5 | Diethylaminoethyl dextran | 2.63% | 42 |

The reaction mixture consisted of 6.0 M ammonia, 240 mM cinnamate, R. glutinis cells and the above described polyhydric alcohol at pH 11.5 and 37° C. The final concentration of R. glutinis cells was approximately 90 mg/ml (wet weight). L-phenylalanine formation was determinted by high pressure liquid chromatography following a 19 hour incubation period.

As shown in Table III, the enzyme activity will vary with the particular polyhydric alcohol selected. It should be noted that all experiments tabulated in Table III were carried out at pH 11.5. While the effect of D-mannitol on L-phenylalanine ammonia-lyase enzyme was small at pH 11.5, prior experiments with glycerol indicate that the effect of D-mannitol, as well as other polyhydric alcohols, can be optimized by adjusting the reaction mixture pH between the reported enzyme operability limits of about 9 and 12. While monohydric and dihydric alcohols such as methanol, ethanol, butanol and ethylene glycol were found not to generate the stabilizing effect of this invention, the polymeric dihydric alcohol polyethylene glycol-(400) did exhibit a relative effect of 154 at 0.19 M for the experiment summarized in Table III. It should be recognized that other compounds similar to polyethylene glycol-(400) such as polypropylene glycol and polyethylene glycol-(300) will likely provide the disclosed advantageous results and should be considered equivalents within the scope of the present invention.

In the preferred embodiment of the present invention trans-cinnamate conversion to phenylalanine is further enhanced by immobilizing microbial cells containing L-pheylalanine ammonia-lyase in cross-linked polyethyleneimine coated alginate beads. The polyethyleneimine coated alginate beads containing the microbial cells were prepared according to the method of Birubaum et al., *Biotechnology Letters,* 3, 393–400 (1981), the disclosure of which is hereby incorporated by reference. The microbial cell impregnated beads are further cross-linked and hardened with glutaric dialdehyde as described in Birubaum et al., supra.

Immobilization of the R. glutinis cells, known to have L-phenylalanine ammonia-lyase activity, in alginate beads did not stabilize the phenylalanine ammonia-lyase activity but cross-linking had a significant stabilizing effect. The reaction mixture consisted of cinnamate dissolved in a solution comprising ammonium hydroxide, glycerol and water in a 75:15:10 ratio by volume, respectively. The final cinnamate concentration was 3.9 weight percent. One ml of the reaction mixture was mixed with approximately thirty-five beads (3-4 mm diameter) impregnated with *R. glutinis* cells according to the above described procedure and then incubated at 37° C. for 24 hours. The conversion of trans-cinnamate to L-phenylalanine was determined by high pressure liquid chromatography. The glutaric dialdehyde cross-linked and hardened beads impregnated with *R. glutinis* cells displayed a four-fold increase in the amount of L-phenylalanine formed as compared to the same immobilzed cell system but not cross-linked and hardened with glutaric dialdehyde.

I claim:

1. A process for the synthesis of L-phenylalanines and analogues thereof which comprises reacting trans-cinnamate, ring-substituted trans-cinnamates or acrylate derivatives and ammonia or an ammonia donor in the presence of L-phenylalanine ammonia-lyase enzyme and a polyhydric alcohol or polyethelene glycol-(400).

2. The process of Claim 1 in which the reaction is conducted at a temperature between about 20° C. and 60° C.

3. The process of Claim 1 in which the reaction is conducted at a pH between about 9 and 12.

4. The process of Claim 1 in which the L-phenylalanine ammonia-lyase enzyme is supplied by suitable microbial cells.

5. The process of Claim 1 in which the L-phenylalanine ammonia-lyase enzyme is supplied by suitable plant cells.

6. A process for the synthesis of L-phenylalanine which comprises reacting trans-cinnamate and an ammonia donor in the presence of L-phenylalanine ammonia-lyase enzyme and a polyhydric alcohol or polyethylene glycol-(400).

7. The process of Claim 6 in which the reaction is conducted at a temperature between about 30° C. and 40° C.

8. The process of Claim 6 in which the reaction is conducted at a pH between about 11.0 and 11.5.

9. The process of Claim 6 in which the trans-cinnamate concentration is between about 100 mM and 300 mM.

10. The process of Claim 6 in which the polyhydric alcohol is selected from the group consisting of glycerol, D-mannitol, D-sorbitol, diethylaminoethyl-dextran.

11. The process of Claim 4 in which the L-phenylalanine ammonia-lyase active microbial cells are immobilized within polyethyleneimine coated alginate beads.

12. The process of Claim 5 in which the L-phenylalanine ammonia-lyase active plant cells are immobilized within polyethyleneimine coated alginate beads.

13. The process of Claim 11 in which the beads are cross-linked and hardened with glutaric dialdehyde.

14. The process of Claim 12 in which the beads are cross-linked and hardened with glutaric dialdehyde.

15. The process of Claim 1 in which para-coumaric acid is aminated to obtain L-tyrosine.

16. The process of Claim 1 in which caffeic acid is aminated to form 3,4-dihydroxyphenylalanine.

17. A process for the synthesis of L-phenylalanine which comprises reacting trans-cinnamate and ammonia in the presence of L-phenylalanine ammonia-lyase enzyme and glycerol, at a temperature ranging from about 20° C. to about 60° C. and a pH ranging from about 9 to 12.

18. The process of Claim 17 in which *Rhodotorula glutinis* cells supply the L-phenylalanine ammonia-lyase enzyme for the reaction.

* * * * *